(12) United States Patent
Schreiber et al.

(10) Patent No.: US 7,087,585 B2
(45) Date of Patent: Aug. 8, 2006

(54) TRIPEPTIDE OF FCγRIIA

(75) Inventors: Alan D. Schreiber, Philadelphia, PA (US); Randall Worth, Philadelphia, PA (US); Howard R. Petty, Detroit, MI (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 277 days.

(21) Appl. No.: 09/989,298

(22) Filed: Nov. 21, 2001

(65) Prior Publication Data

US 2002/0127209 A1 Sep. 12, 2002

Related U.S. Application Data

(60) Provisional application No. 60/252,460, filed on Nov. 22, 2000.

(51) Int. Cl.
*A61K 31/00* (2006.01)

(52) U.S. Cl. .................. 514/44; 536/23.1; 536/23.5; 435/69.1; 435/455; 435/458

(58) Field of Classification Search .............. 514/44; 536/23.1, 23.5; 435/69.1, 455, 458
See application file for complete search history.

(56) References Cited

U.S. PATENT DOCUMENTS 5,776,910 A * 7/1998 Schreiber et al.

6,068,983 A * 5/2000 Schreiber et al.

FOREIGN PATENT DOCUMENTS

WO    WO 95/09002    4/1995

OTHER PUBLICATIONS

Worth et al, "The cytoplasmic domain of FcgammaRIIA (CD32) participates in phagolysosome formation", Blood 98(12):3429–3434 (2001)—Abstract.

Downey et al, "Phagosomal Maturation, Acidification, and Inhibition of Bacterial Growth in Nonphagocytic Cells Transfected with FcγRIIA Receptors", The Journal of Biological Chemistry 274(40):28436–28444 (1999).

Ortalo–Magné et al, "Identification of the Surface–Exposed Lipids on the Cell Envelopes of *Mycobacterium tuberculosis* and Other Mycobacterial Species", Journal of Bacteriology 178(2):456–461 (1996).

Mitchell et al, "Substitutions and Deletions in the Cytoplasmic Domain of the Phagocytic Receptor FcγRIIA; Effect on Receptor Tyrosine Phosphorylation and Phagocytosis", Blood 84(6):1753–1759 (1994).

* cited by examiner

*Primary Examiner*—Robert A. Zeman
(74) *Attorney, Agent, or Firm*—Nixon & Vanderhye P.C.

(57) ABSTRACT

The present invention relates, in general, to phagocytosis and phagolysosomal fusion and, in particular, to a tripeptide of FcγRIIA that mediates trafficking of targets phagocytosed via FcγRIIA to the lysosomal compartment.

6 Claims, 5 Drawing Sheets

TRIPEPTIDE OF FCγRIIA

This application claims priority from Provisional Application No. 60/252,460, filed Nov. 22, 2000, the entire content of which is incorporated herein by reference.

TECHNICAL FIELD

The present invention relates, in general, to phagocytosis and phagolysosomal fusion and, in particular, to a tripeptide of FcγRIIA that mediates trafficking of targets phagocytosed via FcγRIIA to the lysosomal compartment.

BACKGROUND

Phagolysosome fusion is an important pathway in the degradation of internalized particles. Once a particle is internalized by phagocytosis it is directed toward the lysosomal compartment for degradation. Various studies have traced this sequence of events from binding and phagocytosis to eventual trafficking to lysosomes. In addition, the signaling machinery needed to perform many of these activities has been described. Recently, intracellular tyrosine-based activation motifs (ITAM) have taken center stage in the initiation and propagation of activation signals of phagocytic receptors.

ITAM motifs contribute to the ability of phagocytic receptors to efficiently internalize particles (Tuijnman et al, Blood 79:1651 (1992), Mitchell et al, Blood 84:1753 (1994)). ITAM motifs are composed of two YXXL motifs separated by a string of various amino acids. This motif forms a SH-2 binding domain for docking of signaling proteins such as Src and Syk, among others (Isakov Immunol. Res. 16:85 (1997), Isakov, J. Leuko. Biol. 61:6 (1997)). Specifically, upon ITAM phosphorylation, FcγRIIA has been shown to signal through Syk (Indik, et al, Blood 86:4389 (1995), Matsuda et al, Mol. Bio. Cell 7:1095 (1996)). In addition, mutation of either of the ITAM tyrosines abolishes the phagocytic activity of FcγRIIA (Mitchell et al, Blood 84:1753 (1994)). These YXXL sequences can also associate with adaptor proteins such as AP-1 and AP-2 in forming clathrin cups during phagocytosis.

Once a target is internalized, it can be sent to the lysosomal compartment for degradation. Di-leucine motifs in the cytoplasmic domain of various receptors are responsible for the trafficking of targets from phagosomes to lysosomes (Mayorga et al, J. Biol. Chem. 266:6511 (1991), Hunziker and Fumey, EMBO J. 13:2963 (1994), Letournier and Klausner, Cell 69:1143 (1992)). This motif is present in many receptors such as FcγRIIB, the LDL receptor, and the mannose 6-phosphate receptor (Matter et al, J. Cell Biol. 126:991 (1994), Johnson et al, J. Biol. Chem. 267:17110 (1992)). Mutation of either or both of the leucine residues in these receptors significantly reduces or abolishes lysosomal delivery, respectively.

FcγRIIA mediates phagocytosis through an ITAM motif and also mediates phagolysosomal fusion (Mitchell et al, Blood 84:1753 (1994)). However, there is no consensus di-leucine motif located in the cytoplasmic domain of FcγRIIA. Therefore, another sequence in the cytoplasmic domain of FcγRIIA must participate in lysosomal trafficking. The present invention relates to that sequence.

SUMMARY OF THE INVENTION

The present invention relates to a tripeptide of FcγRIIA that mediates trafficking of targets phagocytosed via FcγRIIA to the lysosomal compartment.

Objects and advantages of the present invention will be clear from the description that follows.

Mutation of either or both leucines in the Y3LTL sequence of the FcγRIIA ITAM inhibits phagolysosomal fusion but does not inhibit phagocytosis of EA. It has been previously demonstrated that FcγRIIA in the absence of ITAM tyrosines (Y2FY3F) does not mediate phagocytosis. However, phagocytosis of EA is partially restored for Y2FY3F by co-transfection with the complement receptor type 3 (CR3) (Worth et al, J. Immunol. 157:5660–5665 (1996)) as demonstrated in column 6. In co-transfected cells, Y2FY3F and CR3 interact and EA bound to Y2FY3F are phagocytosed through the cytoplasmic domain of CR3. 78% of the ingested EA mediated by CR3 and Y2FY3F co-localized with lysosomes (column 6), indicating that the ITAM tyrosines do not play a significant role in phagolysosomal fusion. Significant inhibition of phagolysosomal fusion (p<0.001) was observed for the mutants Y3ATL, Y3LTA and Y3ATA, while the ingestion of EA (phagocytosis) was unaltered (columns 3–5). Thus the LTL sequence of the FcγRIIA cytoplasmic domain targets the phagosome for fusion with lysosomes whereas the tyrosines of the ITAM sequence are essential for the initial stage of phagocytosis.

Figure 2:
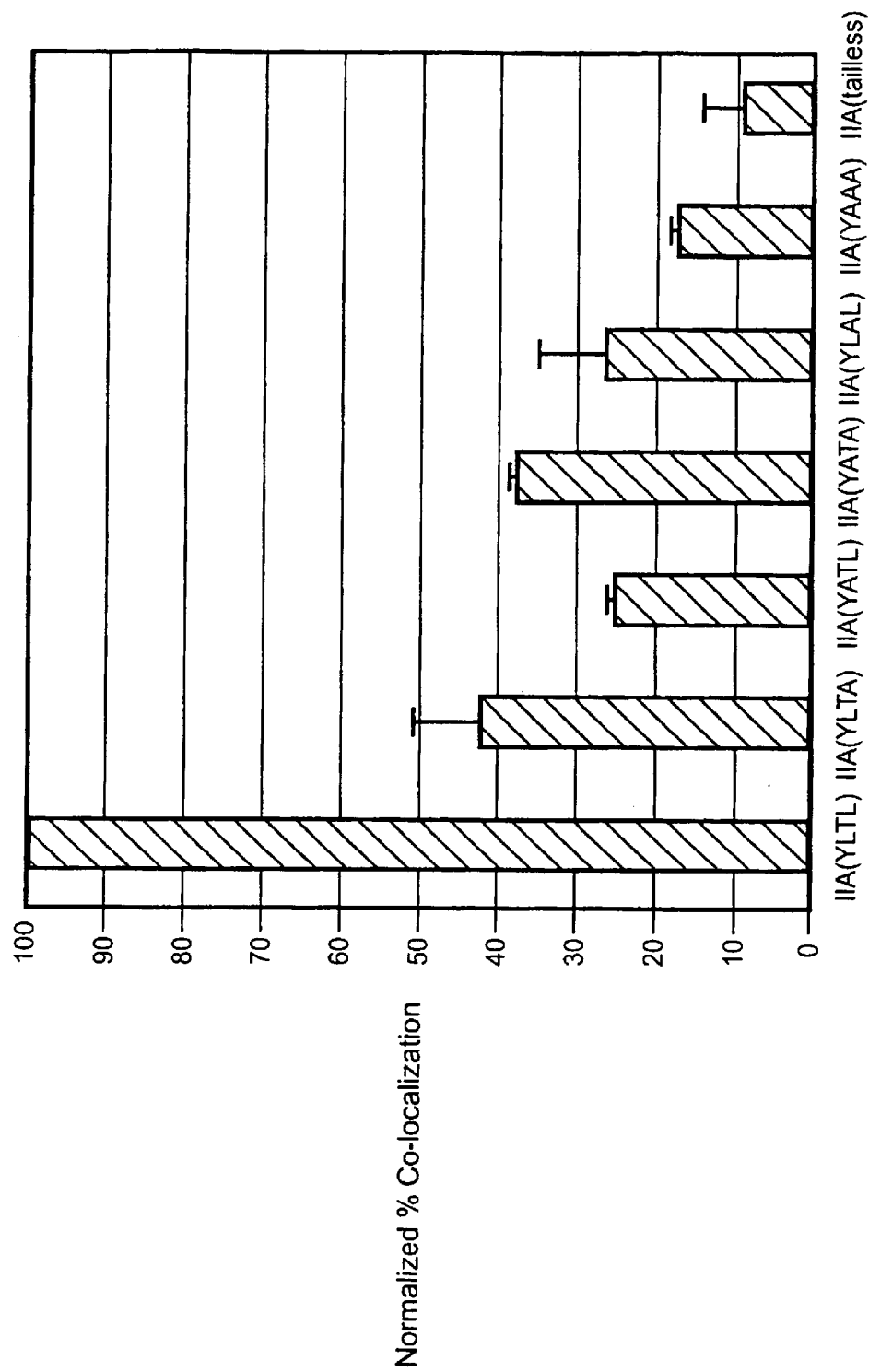

FIG. 2. Mutation of the novel L-T-L motif in the cytoplasmic domain of FcγRIIA inhibits phagolysosome fusion.

Figure 3:
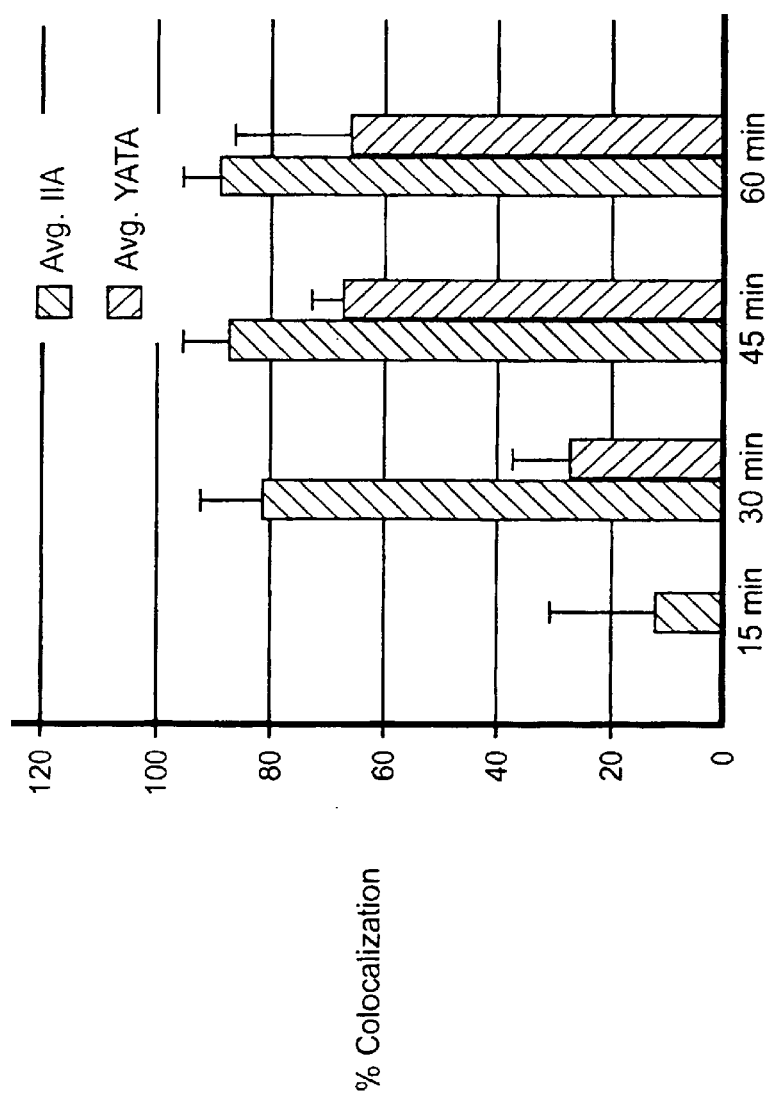

FIG. 3. L-T-L motif mediates specific targeting of internalized targets to fuse with lysosomes.

Figure 4:
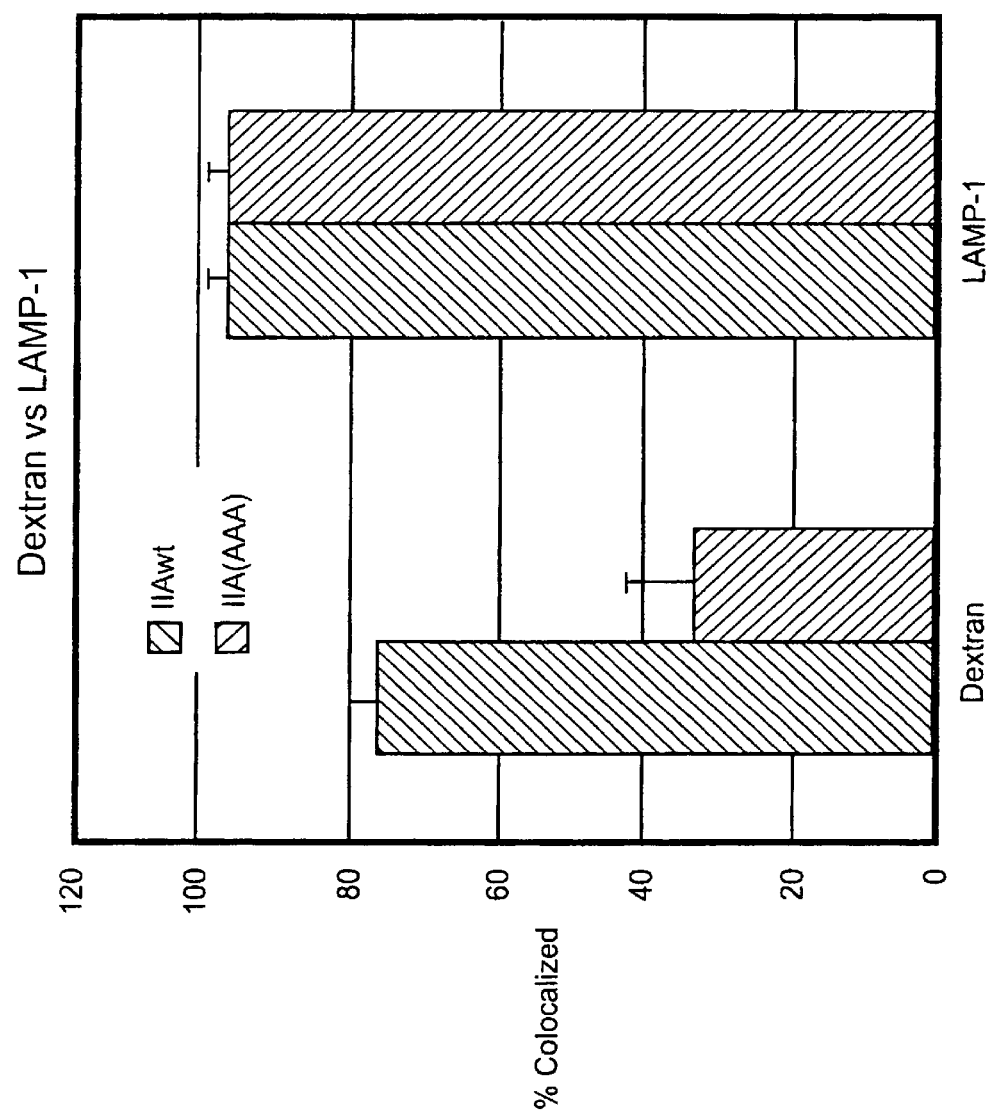

FIG. 4. L-T-L motif inhibits fusion events leading to phagolysosome formation but not protein colocalization.

Figure 5:
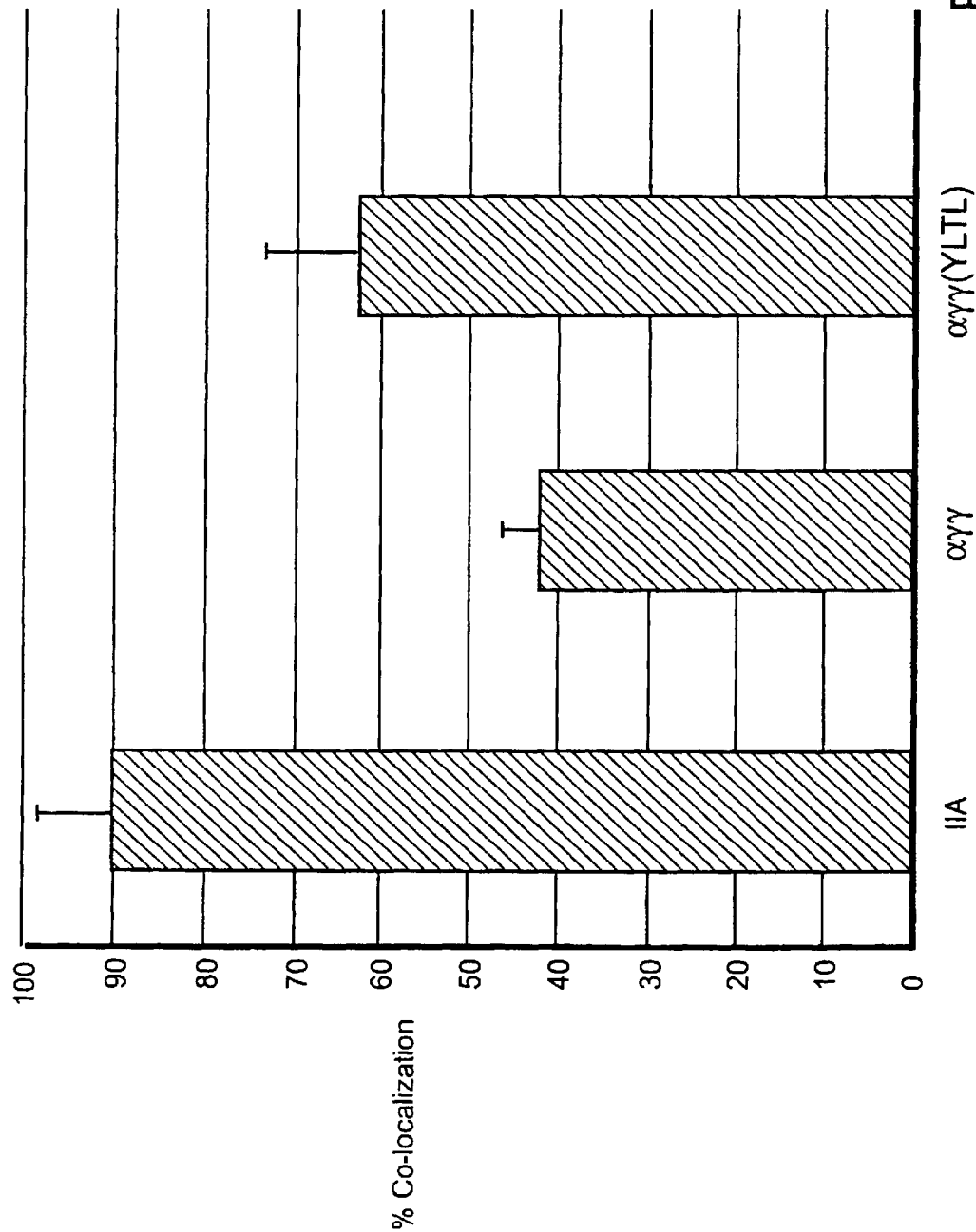

FIG. 5. Inserting the L-T-L motif into a receptor that normally does not mediate efficient phagolysosome formation increases the ability to form phagolysosomes.

DETAILED DESCRIPTION OF THE INVENTION

The present invention is based on the realization that the cytoplasmic domain of FcγRIIA mediates lysosome fusion subsequent to phagocytosis. This L-T-L motif is found at the C-terminal of the ITAM motif of FcγRIIA.

Chinese hamster ovary (CHO) cells provide a good model system for studying phagocytosis and intracellular trafficking. CHO cells transiently transfected with FcγRIIA bind and internalize IgG-coated targets efficiently. Internal targets can be differentiated from bound targets by the addition of a fluorescent secondary goat anti-rabbit IgG. The second step antibody binds only to bound targets thus discriminating between bound and internal targets. In addition, FcγRIIA has been shown to mediate lysosomal fusion by observing the co-localization of pre-loaded fluorescent dextran, which accumulates in lysosomes, with the target when viewed with fluorescence microscopy.

FcγRIIA mediated lysosome fusion does not require an intact ITAM motif. Previously described studies have shown that mutation of either of the tyrosine residues in the ITAM motif of FcγRIIA abolishes phagocytosis (Mitchell et al, Blood 84:1753 (1994)). Because mutation of the two tyrosine residues abolishes phagocytosis, the genetic complementation ability of complement receptor type 3 (CR3) was utilized. CR3 has previously been shown to rescue the phagocytic activity of mutated FcγRIIA (Worth et al, J. Immunol. 157:5660 (1996)). FcγRIIA with mutations of tyr→phe is able to mediate lysosomal delivery of targets phagocytosed through the complementary activity of CR3 (which itself does not mediate lysosomal fusion). Mutation of the two tyrosine residues comprising the ITAM abolishes the phagocytic activity of FcγRIIA. However, in the presence of CR3, phagocytosis is restored and over 90% of those internalized targets are delivered to lysosomes. These data indicate that lysosomal delivery is a distinctly separate signal from that involved in phagocytosis and is not dependent on an active ITAM motif.

That lysosomal trafficking and phagocytosis are separate signals is confirmed by mutating the L-T-L sequence of FcγRIIA and observing the ability of internalized targets to be delivered to lysosomes. Firstly, mutation of any or all of these residues does not significantly affect the phagocytic activity of FcγRIIA. Secondly, mutation of either or both of the leucine residues effectively inhibits 70% of internalized particles from fusing with lysosomes. In addition, mutation of the threonine residue alone reduces the lysosomal targeting capacity of FcγRIIA by nearly 70%. However, mutation of all three of these residues does not affect phagocytosis but decreases the lysosomal delivery ability to that of a tailless mutant FcγRIIA.

A similar receptor was also studied that does not contain a di-leucine or L-T-L motif. The γ chain utilized by various Fc receptors such as FcγRI and FcγRIIIA, was utilized. A chimeric FcγRIIIA was formed containing the extracellular domain of FcγRIIIA and the transmembrane and cytoplasmic domains of the γ chain. This chimeric receptor containing the γ chain signaling machinery is not able to target internalized phagocytosed particles to lysosomes. The ITAM motif of the γ chain was then mutated to contain a L-T-L motif and lysosomal delivery ability studied (FIG. 5). In the presence of the L-T-L motif, the γ chain is able to target internalized particles to lysosomes. This study shows that lysosome targeting ability can be transferred to other receptors by translocating this L-T-L motif.

The L-T-L motif in the cytoplasmic domain of FcγRIIA thus mediates lysosome fusion. FcγRIIA-mediated phagocytosis and lysosomal trafficking are composed of two distinct steps mediated by individual signaling motifs. Separate and distinct signals used to mediate internalization and targeting has previously been proposed for the CD3 chains of the T-cell receptor (Letourneur and Klausner, Cell 69:1143 (1992)). The studies described herein confirm that these signals can be distinct, independently acting moieties. The activities of various secondary signal molecules such as Syk, Rac, Rab, and Rho have all been implicated in endosomal/lysosomal dynamics. Further studies are needed to show which signaling molecules are required for various steps of the internalization pathway. These activities may involve a relay type interaction whereby upon receptor activation by phosphorylation, Syk or another kinase can bind. Once Syk is released, the signal may propagate further by activation of Rac/Rab/Rho or another molecule directing the particle to the lysosomal compartment.

The demonstration that the L-T-L motif in the cytoplasmic domain of FcγRIIA is responsible for mediating phagolysosomal fusion makes possible gene therapy strategies whereby a sequence encoding naturally occurring FcγRIIA or a modified form of FcγRIIA (e.g., a form modified so as to include more than one L-T-L motif (e.g., 2 or 3 L-T-L motifs) is transferred into target cells that either normally express FcγRIIA or cells that do not normally express FcγRIIA but that can be effective in cleaning, for example, bacterial infections. Examples of target cells include endothelial cells, fibroblasts, macrophage and epithelial cells (such as hepatocytes and bronchial epithelial cells). The receptor encoding sequence can be administered as naked DNA, in a liposome or bacterium or it can be present in a vector, e.g., a viral vector such an adenoviral or adenoassociated vector or a retroviral vector.

The demonstration that the L-T-L motif in the cytoplasmic domain of FcγRIIA is responsible for mediating phagolysosomal fusion also makes it possible to alter the sequences of Fc receptors, naturally incapable of mediating phagolysosomal fusion, so that they possess that activity. Transferring the L-T-L motif to such receptors (e.g., receptors for mycobacterium including CR3 toll-like receptors, etc.) can increase the efficiency of bacterial killing. Sequences encoding such receptors can be used in gene therapy regimens, as described above.

More specifically, the Fc receptor γ chain by itself does not efficiently mediate phagolysosomal fusion; however, when an L-T-L sequence is inserted into its cytoplasmic domain, it mediates phagolysosomal fusion with increased efficiency (FIG. 5). Thus, in such a manner, receptors that do not mediate phagolysosomal fusion can be induced to do so. As indicated above, Fc receptors can also be altered so as to enhance their natural ability to mediate phagolysosomal fusion. For example, FcγRIIA, upon addition of further L-T-L sequences to the cytoplasmic domain, becomes more potent and efficient in mediating phagolysosomal fusion. (Increasing the number of FcγRIIA molecules (e.g., by administering a biologically active molecule) can be used as an alternative means of increasing the number of L-T-L sequences.) These approaches can be usefully applied for enhancing the killing of bacteria, fungi and other microorganisms (e.g., pyrogenic bacteria such as *E. coli, S. aureus* and *P. aeruginosa*). Some microorganism survive intracellularly, such as mycobacterium, leishmania and listeria. Enhancing phagolysosomal fusion of these antibody coated microorganisms is useful in controlling the growth and killing of these microorganisms.

In addition to mycobacterium, fungi and other bacteria, the anthrax bacterium can also be targeted to increase the efficiency of its (*B. anthracis*) being killed. For example, the uptake of anthrax spores by FcγRIIA or another cell receptor can be induced to undergo phagolysosomal fusion.

The demonstration that the L-T-L motif is responsible for mediating phagolysosomal fusion also makes apparent the advantage of targeting microbes to FcγRIIA using therapeutic strategies involving, for example, the use of a bi-specific antibody that recognizes the target microbe and the extracellular domain of FcγRIIA specifically.

The invention further relates to methods of inducing FcγRIIA uptake and targeting of a microorganism or other particle (e.g., an immune complex) to phagolysosomes of macrophages and other leukocytes. In accordance with this method, IgG antibody directed at the microorganism (e.g., bacterium, including antibiotic resistant *E. coli, Staphylococcus,* etc, mycobacterium, anthrax bacterium, (e.g., *Bacillus anthracis* or *B. anthracis* spores) is administered. The antibody used can be an IgG antibody that recognizes the microorganism and that has associated therewith an L-T-L containing peptide.

The invention also relates to methods of increasing the number of FcγRIIA molecules per macrophage or leukocyte. Certain small molecules can be used to effect the increase, as can IFN-γ or IL-4 inhibitor or cytokine that inhibits the release or action of IL-4.

The invention further relates to a method of facilitating targeting of a microorganism to the phagolysosome by administering an L-T-L containing peptide in a manner such that it associates with the microorganism. A liposome containing or otherwise associated with an L-T-L containing peptide can be injected IV or in some other manner such that it is targeted to macrophages/leucocytes.

In accordance with the invention, Fc receptors naturally capable of mediating phagolysosomal fusion can be rendered incapable of such mediation. This can be accomplished using peptide mimetics or small molecule (organic) mimetics that function as inhibitors of the L-T-L sequence. This approach is advantageous when it is desirable to inhibit phagolysosomal fusion, for example, in the preservation of antibody and immune complexes and in hindering their degradation.

Receptors as indicated above (including modified receptors) and L-T-L containing peptides (and respective encoding sequences) can be administered using techniques described, for example, in U.S. Pat. Nos. 6,608,983, 5,858,981, 5,821,071, 5,776,910, 5,641,875, and 5,641,863.

Certain aspects of the invention can be described in greater detail in the non-limiting Examples that follows. The following references include details of the receptor structures and encoding sequences: Schreiber et al, Clin. Immunol. Immunopath. 62:S66 (1992), Cassel et al, Molec. Immunol. 30:451 (1993), Allen et al, Science 243:378 (1989), Letourner et al, J. Immunol. 147:2652 (1991), Ra et al, Nature (Lond.) 241:752 (1989), Park et al, Clin. Res. 41:324A (1993), Simmons et al, Nature 333:568 (1988).

EXAMPLE 1

Cytoplasmic Domain of FcγRIIA (CD32) Participates in Phagolysosomal Formation

Experimental Details

Cell Culture and Transfections

Chinese hamster ovary (CHO) cells were transfected by electroporation with a mixture of 1.5 μg of pSVneo, 5 μg of pBACD11b (generated by replacing the CD11a cDNA in pBACD11a (Krauss, Hum. Gene Ther. 2:221 (1991)) with the CD11b cDNA (Hickstein et al, Proc. Natl. Acad. Sci. USA 86:257 (1989)), 5 μg of pCMVBACD18, and 5 μg of either pRcCMVCD32 or a variant of this CD32 plasmid containing a tail-minus mutation, as described (Xue, et al, J. Immunol. 152:4630 (1994)). Expansion and selection were performed as previously described (Worth et al, J. Immunol. 157:5660 (1996)). Six different clones were generated: 161-24 which was not transfected but exposed to the transfection protocol; 161-84 expressed only CR3; 131-3 which expressed wild type FcγRIIA; 135-12 expresses FcγRIIA tailless alone; 169-8, 169-24 which both express the FcγRIIA tailless and the α and γ chains of CR3; and 173-46 expressing both the wild-type FcγRIIA and CR3. In addition, variants expressing a full length FcγRIIA cytoplasmic domain with tyrosine→phenylalanine mutations in both of the ITAM motifs (FcγRIIA ITAM mutant) were transiently transfected into an untransfected CHO cell line (labeled clone 161-30) or a CR3 expressing CHO cell line (labeled clone 169-85) using DEAE dextran or FuGene6 transfection reagent. For experiments, cells were seeded onto 25 $mm^2$ coverslips and allowed to adhere overnight at 37° C. in 5% $CO_2$. Cells were tested for expression using both indirect immunofluorescence flow cytometry and fluorescence microscopy as previously described (Worth et al, J. Immunol. 157:5660 (1996)).

Lysosome Labeling

Transfectants were grown on glass coverslips (Corning, N.Y.) overnight at 37° C. 5 μg of rhodamine-conjugated dextran (10,000 MW, Molecular Probes, Eugene, Oreg.) was added to each coverslip for 90 min. at 37° C. Cells were washed with PBS followed by addition of fresh media to the coverslips as described by Oh and Swanson (Oh and Swanson, J. Cell Biol. 132:585 (1996)). Imaging of lysosomes was performed using an axiovert 135 fluorescence microscope (Carl Zeiss, Thornwood, N.Y.) utilizing mercury illumination. Optical filters for rhodamine excitation and emission were 530DF22 and 590DF30, respectively (Omega, Brattlesboro, Vt.). Images were observed using an ICCD (Hamamatsu, Japan) coupled to a Scion LG-3 (Scion Corp., Frederick, Md.) image capture board on a Dell Precision 410 Workstation (Round Rock, Tex.). Images were processed using Scion Image software.

Phagocytosis of Erythrocytes

SRBCs (Alsevers; Rockland Scientific, Gilbertsville, Pa.) were opsonized with the highest subagglutinating concentration of rabbit anti-sheep erythrocyte Ab (ICN, Costa Mesa, Calif.). Subsequently, antibody coated cells (EA) were added at a target-to-effector ratio of 10:1 (EA:transfectant). The EA were incubated with transfectants for 45 min. at 37° C. in culture media. Coverslips were then placed on ice to stop phagocytosis.

Fluorescence Microscopy

Goat anti-rabbit IgG F(ab')$_2$ fragments conjugated with fluorescein isothiocyanate (ICN, Costa Mesa, Calif.) were added to the coverslips for 30 min. on ice to detect the external EA. The coverslips were observed using bright field microscopy or by fluorescence microscopy using the system described above. Narrow band-pass discriminating filters were used with excitation at 482 nm and emission at 530 nm for FITC fluorescence.

Electron Microscopy

Transfectants expressing either wild type FcγRIIA (131-3) or tailless FcγRIIA with CR3 (169-23) were incubated with opsonized sheep erythrocytes for 45 min. at 37° C. in culture media. The cells were washed then fixed with glutaraldehyde overnight at 4° C. To detect the lysosomal compartment, acid phosphatase was stained for using modified Gormori's media consisting of 13.9 mM β-glycerophosphate, 1 mM $Pb(NO_3)_2$, 0.05 M acetate buffer, 0.08% $CaCl_2$, and 5% sucrose. Cells were treated with the acid phosphatase stain for 1 hr at 37° C. with gentle agitation. The cells were washed extensively with cacodylate buffer then post-fixed with osmium tetroxide for 1 hr at room temperature. The cells were dehydrated and embedded in Spurr's resin as described previously (Spurr, J. Ultrastruct. Res. 26:31 (1969)). Thin-sections were viewed with a Joel 35e (Japan) electron microscope. Micrographs were taken using an in-column digital camera system coupled to a Macintosh G3 computer and processed with Adobe photoshop 5.0.

Results

Receptor Expression and Phagocytosis

Transfected CHO cells were studied for expression of FcγRIIA and CR3 utilizing flow cytometry. Several cell lines were produced. Clone 131-3 expressed wild-type FcγRIIA. 135-12 expressed the tail-minus mutant of FcγRIIA. 161-24 expressed neither of the receptors but was exposed to the transfection protocol. Clones 169-8 and 169-23 both expressed the tailless mutant FcγRIIA in combination with CR3. A wild-type FcγRIIA and CR3 clone (173-46) were also constructed. Indirect immunofluorescence analysis confirmed the phenotypes of the cell lines. In addition, a phagocytosis defective FcγRIIA was utilized that had a full length cytoplasmic domain with only the tyrosine residues in each of the ITAM motifs mutated to phenylalanine (FcγRIIA ITAM mutant). This mutation has previously been shown to abolish IgG-dependent phagocytosis via FcγRIIA Mitchell et al, Blood 84:1753 (1994)). FcγRIIA(ITAM mutant) was transiently transfected into untransfected CHO cells (161-30) or a CR3 expressing cell line (169-85). Expression was determined via indirect immunofluorescence quantitated by flow cytometry. Expression of wild-type FcγRIIA and this FcγRIIA(ITAM mutant) were equivalent.

To confirm that the receptors were functional, phagocytosis was examined using IgG-coated sheep erythrocytes (EA). After incubation of EA with the transfectants for 30 min. at 37° C., it was found that the wild-type FcγRIIA (clone 131-3) was capable of internalizing IgG-coated erythrocytes. However, the FcγRIIA tailless (clone 135-12) and the FcγRIIA(ITAM mutant) (clone 161-30) were not able to phagocytose EA, as previously reported (Tuijnman et al, Blood 79:1651 (1992), Mitchell et al, Blood 84:1753 (1994), Worth et al, J. Immunol. 157:5660 (1996)). However, the co-expression of CR3 with either of the mutant FcγRIIAs (clones 169-8, 169-23 and 169-85) restored FcγR-dependent phagocytosis.

Fluorescence detection of phagosome-lysosome fusion

It was next determined whether the cytoplasmic tail of FcγRIIA participates in phagolysosomal fusion. Fluorescently-labeled dextran was used to label lysosomes Oh and Swanson, J. Cell Biol. 132:585 (1996)). Fluorescent dextran is taken up by pinocytosis then delivered to lysosomes. This allows the fluorescent dextran to spill from the pre-loaded lysosomes into the phagosome. After incubation with dextran, the transfectants exhibited dextran located in small punctate vesicles when viewed with fluorescence microscopy.

Previous work has shown that co-expression of CR3 and a phagocytosis defective tailless FcγRIIA restored IgG-dependent phagocytosis (Worth et al, J. Immunol. 157:5660 (1996)). This approach was used, co-transfection of FcγRIIA and CR3, to examine post-phagocytic events in the presence and absence of the cytoplasmic tail of FcγRIIA or in an ITAM mutant of FcγRIIA. Wild-type FcγRIIA (clone 131-3) transfectants exhibited co-localization of fluorescent dextran with the internalized IgG-coated particle. This effect was seen as soon as 15 min. after addition of targets and did not change significantly up to 60 min. after phagocytosis. In addition, more than 95% of the internalized targets were positive for lysosome fusion. However, when the cell lines containing the mutant tailless form of FcγRIIA in the presence of CR3 were studied (clones 169-8 and 169-23), very little co-localization of IgG-coated cells with the dextran was observed. Little or no co-localization of dextran with EA was observed from 15 min. to 60 min. after phagocytosis. Internalized targets displayed fusion with lysosomes in 6.4% and 8.7% of the cells for clones 169-8 and 169-23, respectively. These results were observed in two separate clones, suggesting consistency among similarly prepared clones. The FcγRIIA ITAM mutant (161-30) without CR3 is unable to induce phagocytosis of IgG-coated cells and therefore no lysosomal fusion can occur. However, in the presence of CR3 and FcγRIIA ITAM mutant (169-85), phagocytosis was restored and near wild type levels of lysosome fusion was detected. Clone 173-46, which expressed wild-type FcγRIIA and CR3, to determine if CR3 might affect phagolysosome formation. Expression of CR3 did not affect the ability of wild-type FcγRIIA to participate in phagolysosome fusion.

Electron Microscopy of Phagosome-lysosome Fusion

As a second independent means of detecting phagosome-lysosome fusion following phagocytosis, electron microscopy was employed using a specific lysosomal stain. Acid phosphatase is an enzyme specific for lysosomes and has been used extensively to stain CHO cells (Gennaro et al, Proc. Soc. Exp. Biol. Med. 198:591 (1991)). Therefore, this enzyme was used to detect the localization of lysosomal enzymes inside cells. After incubation of transfectants expressing either wild type FcγRIIA or tailless FcγRIIA in the presence of CR3 with IgG-coated sheep erythrocytes, the cells were fixed and stained for acid phosphatase. After embedding, thin sections were viewed with an electron microscope. Acid phosphatase appeared as dark electron dense patches, revealing the location of lysosomal enzyme activity. In the presence of the wild-type FcγRIIA (clone 131-3) acid phosphatase staining was observed near the internalized target, indicating phagolysosomal fusion. However, cells expressing the tail-minus form of FcγRIIA (clone 169-8) did not support phagolysosome formation. Thus, the acid phosphatase staining was found throughout the entire cytoplasm as punctate granules and was not localized near internalized targets. These results suggest that the cytoplasmic domain of FcγRIIA targets the internalized particle for fusion with lysosomes. The data demonstrate that the cytoplasmic tail of FcγRIIA participates in phagolysosomal fusion and that this signal is distinct from a functional ITAM.

EXAMPLE 2

Lysosomal Fusion Following FcγRIIA Phagocytosis is Mediated by an L-T-L Motif

Figure 1:
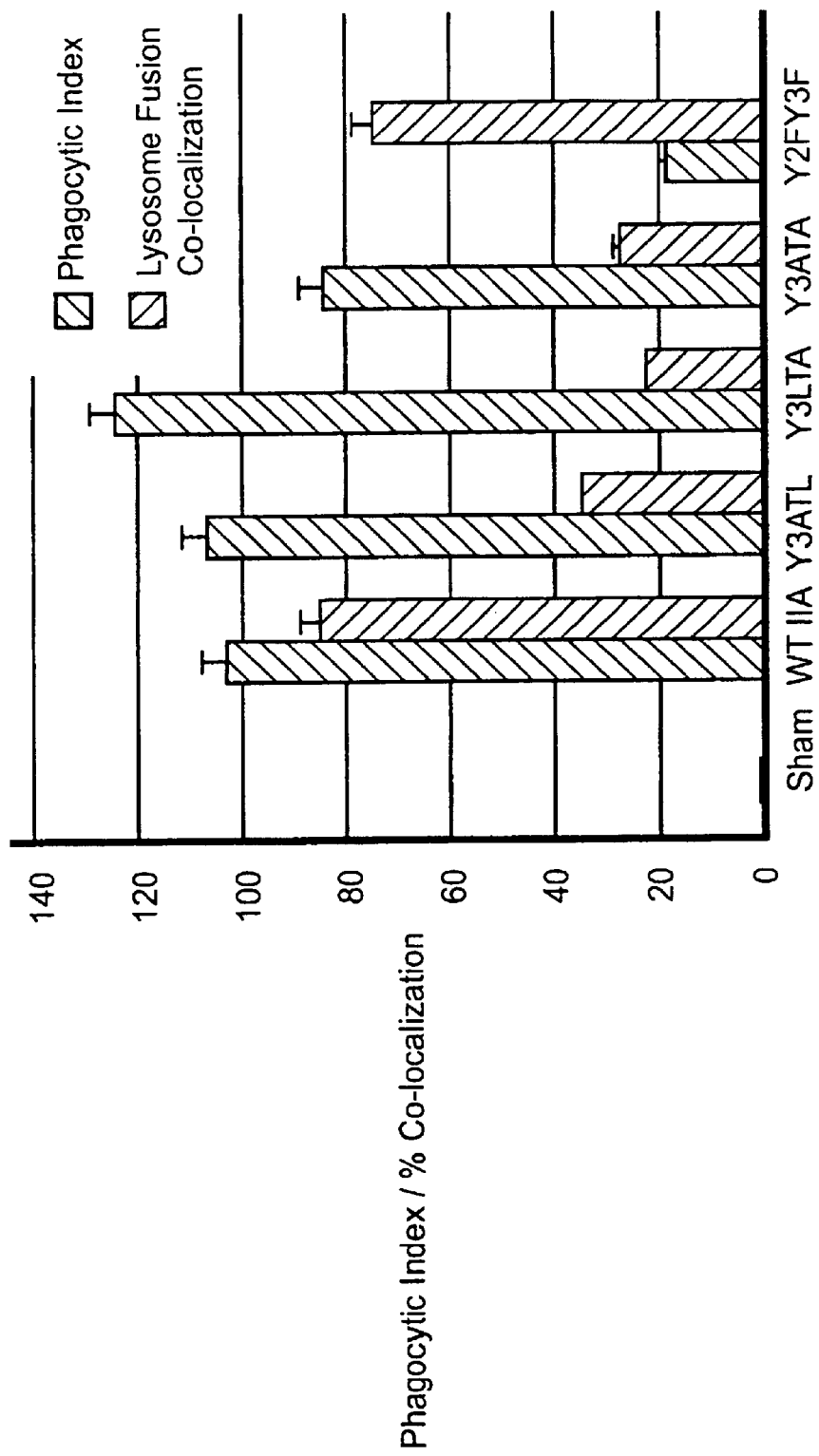
FIG. 1. A distinct FcγRIIA cytoplasmic domain sequence determines phagolysosomal fusion. CHO cells were transfected with WT FcγRIIA (WT IIA, column 2) or with mutants of the FcγRIIA cytoplasmic ITAM. Wt IIA contains the ITAM sequence Y2MTL-Y3LTL. The FcγRIIA mutants contain the following ITAM sequences: Y2MTL-Y3ATL (designated Y3ATL, column 3), Y2MTL-Y3LTA (designated Y3LTA, column 4), Y2MTL-Y3ATA (designated Y3ATA, column 5) or F2MTL-F3LTL (designated Y2FY3F, column 6) (Y=tyrosine, M=methionine, T=threonine, L=leucine, A=alanine, F=phenylalanine). After 48 hrs, the transfected cells were loaded with rhodamine conjugated dextran and then incubated with IgG coated RBCs (EA). Following removal of externally bound EA, the phagocytic index (PI), the number of internalized EA/100 cells, was determined by bright field microscopy. Lysosomes labelled with rhodamine conjugated dextran were visualized by fluorescence microscopy. Phagolysosome fusion was analyzed by determining the co-localization of EA and rhodamine dextran and expressed as % co-localization. Column 1 represents sham transfected cells.

This study was designed to elucidate the mechanism by which FcγRIIA mediates lysosomal fusion. As indicated in Example 1, a mutant FcγRIIA lacking a cytoplasmic domain is not able to mediate phagocytosis. However, the presence of complement receptor type 3 (CR3) restores phagocytosis, but no lysosomal fusion is observed. Therefore, the cytoplasmic domain of FcγRIIA is required for lysosomal fusion. The FcγRIIA cytoplasmic domain ITAM (immunoreceptor tyrosine-based activation motif) was disabled to determine if an intact ITAM is required for lysosomal targeting. Mutation of both tyrosines in the ITAM to phenylalanine abolished phagocytosis. However, co-transfection of CR3 with this ITAM mutant restored phagocytosis and wild-type (WT) levels of lysosomal fusion were observed. After mutation of signaling sequences in the cytoplasmic domain of FcγRIIA, it was noted that a novel L-T-L motif at the C-terminal of the ITAM was responsible for targeting of FcγRIIA internalized targets to the lysosomal compartment, but not required for the initial stage(s) of phagocytosis. Mutation of either of the leucine residues individually or in tandem resulted in 70% (p<0.05 compared to wt FcγRIIA) inhibition of internalized targets to co-localize with lysosomes pre-loaded with fluorescent dextran. Mutation of the threonine alone elicited similar results, thus abolishing 78% (p<0.05 compared to wt FcγRIIA) of co-localization. However, when the L-T-L motif was mutated to A-A-A, lysosomal targeting was abolished as observed with tailless FcγRIIA. Therefore, a novel L-T-L motif in the cytoplasmic domain of FcγRIIA is responsible for mediating phagolysosomal fusion. (See also FIG. 1).

EXAMPLE 3

FcγRIIA wild-type (IIA), various mutants of the L_T-L motif in the cytoplasmic domain of FcγRIIA (IIA(YLTA), IIA(YATL), IIA(YATA), IIA(YAAA)), or FcγRIIA lacking a cytoplasmic domain (IIA(tailless)) were transfected into chinese hamster ovary (CHO) cells. These cells were pre-loaded with fluorescently labeled dextran by incubating the cells with medium containing TRITC-dextran. The cells were then allowed to phagocytose IgG-coated erythrocytes (EA) for 30 minutes. After 30 minutes the cells were placed on ice to stop phagocytosis and observed for location of the internalized EA and TRITC-dextran. Data presented in FIG. 2 are shown as percent of internalized EA colocalized with TRITC-dextran. As shown, mutation of the L-T-L motif inhibits the colocalization (phagolysosome fusion) of the internal EA with TRITC-dextran.

The data presented in FIG. 3 demonstrate that the L-T-L motif mediates specific targeting of internalized targets to fuse with lysosomes. In time-course experiments, the mutant FcγRIIA containing a mutant L-T-L motif, inhibited phagolysosome formation at early time points compared to wild-type FcγRIIA.

To elucidate the mechanism by which the L-T-L motif inhibits phagolysosome fusion, another marker of lysosome location was studied. Lysosome associated membrane protein (LAMP) is a cytosolic protein that colocalizes with lysosomes and the plasma membrane. It was observed that the L-T-L mutation inhibits the spilling of fluorescent dextran into phagosomes but does not inhibit the acquisition of lysosome associated proteins thus suggesting that phagolysosome formation may be a more complex process than originally thought (see FIG. 4).

The common γ-chain does not mediate efficient phagolysosome fusion. A chimeric molecule was produced containing the ligand-binding domain of FcγRIII and the γ-chain transmembrane and cytoplasmic domain. Upon insertion of the L-T-L motif into the cytoplasmic domain of the chimeric molecule, a 50% increase in phagolysosome formation was observed (see FIG. 5). These data indicate that insertion of the L-T-L motif into a receptor that is not efficient in mediating phagolysosomal fusion can be used to increase the ability of receptors to kill bacterium All documents cited above are hereby incorporated in their entirety by reference.

What is claimed is:

1. A method of enhancing the ability of a cell to degrade a particle comprising introducing into said cell a nucleic acid sequence encoding an Fc receptor comprising an L-T-L sequence in a cytoplasmic domain thereof, said introduction being effected under conditions such that said nucleic acid sequence is expressed and said enhancement is thereby effected, wherein said Fc receptor comprises a FcγRIIA cytoplasmic domain modified to comprise at least 1 additional L-T-L peptide.

2. The method according to claim 1 wherein said cell naturally expresses FcγRIIA.

3. The method according to claim 1 wherein said cell does not naturally express FcγRIIA.

4. The method according to claim 1 wherein said cell is an endothelial cell, a fibroblast, a macrophage or an epithelial cell.

5. The method according to claim 1 wherein said particle is a bacterium.

6. The method according to claim 1 wherein said nucleic acid sequence is introduced into said cell in a liposome, a bacterium or a viral vector.

* * * * *